United States Patent [19]

Annapragada et al.

[11] Patent Number: 4,952,547
[45] Date of Patent: Aug. 28, 1990

[54] CATALYST FOR CONVERTING METHANE TO HIGHER HYDROCARBONS, INCLUDING AROMATIC COMPOUNDS

[75] Inventors: Ananth V. Annapragada; Erdogan Gulari, both of Ann Arbor, Mich.

[73] Assignee: The Regents of the University of Michigan, Ann Arbor, Mich.

[21] Appl. No.: 223,619

[22] Filed: Jul. 25, 1988

[51] Int. Cl.$^5$ ............................................. B01J 27/185
[52] U.S. Cl. ..................................... 502/213; 585/500; 585/943
[58] Field of Search ......................... 502/213; 423/305

[56] References Cited

U.S. PATENT DOCUMENTS

| | | | |
|---|---|---|---|
| 2,614,100 | 10/1952 | Uraneck et al. | 526/93 |
| 3,006,975 | 10/1961 | Ryland et al. | 585/444 |
| 3,050,473 | 8/1962 | Morrell | 502/213 |
| 3,142,697 | 7/1964 | Jennings et al. | 558/322 |
| 3,716,545 | 2/1975 | Ripley | 546/352 |
| 3,928,389 | 12/1975 | Farha, Jr. et al. | 502/213 |
| 4,324,908 | 4/1982 | Grasselli et al. | 560/210 |
| 4,427,792 | 1/1984 | Pederson et al. | 502/213 |

Primary Examiner—Paul E. Konopka
Attorney, Agent, or Firm—Oblon, Spivak, McClelland, Maier & Neustadt

[57] ABSTRACT

A catalyst for use in a process for oxidatively coupling methane to $C_2$ and other hydrocarbons, including aromatic hydrocarbons, which is an iron-phosphorus-oxide catalyst having an iron to phosphorus ratio of from 0.1:1.0 to 2.0:1.0 is used.

17 Claims, 1 Drawing Sheet

CATALYST FOR CONVERTING METHANE TO HIGHER HYDROCARBONS, INCLUDING AROMATIC COMPOUNDS

BACKGROUND OF THE INVENTION

1. Field of the Invention:

The present invention relates to processes and catalysts for transforming methane to higher hydrocarbons.

2. Discussion of the Background:

It is the business of many refineries and chemical plants to obtain, process and upgrade relatively low value hydrocarbons to more valuable feeds, or chemical raw materials. Methane, the simplest of the saturated hydrocarbons, is often available in large quantities either as an undesirable by-product in admixture with other more valuable higher molecular weight hydrocarbons, or as a component of an off-gas from a process unit, or units. This methane however, is not fully utilized by the chemical industry because it is expensive to transport and is not readily transformed into a derivative which could be easily transported. Enormous amounts of this natural resource are wasted or left lying unused in remote storage sites due to prohibitive transportation costs.

Natural gas which contains high concentrations of methane is produced in considerable quantities in oil and gas fields, often at remote locations and in difficult terrains, e.g., off-shore sites, artic sites, swamps, deserts and the like. Under such circumstances the natural gas is often flared while the oil is recovered, or the gas is shut in, if the field is too remote for the gas to be recovered on a commercial basis. The construction of pipelines to carry the gas is often not economical, due particularly to the costs of connnecting numerous well sites with a main line.

This problem has been addressed in several ways. One approach has been to liquify the natural gas and transport the liquid natural gas in specially designed tanker ships. Natural gas can be reduced to 1/600th of the volume it occupies in the gaseous state by cryogenic processing, and with proper procedures, safely stored or transported. Transport of natural gas under such circumstances is uneconomical however because methane at atmospheric pressure boils at $-258°$ F. and transportation economics dictate that the gas be liquifiable at substantially atmospheric pressures to reduce its volume.

Another approach to this problem has been the conversion of natural gas to other higher hydrocarbons that can be easily handled and transported, preferably substantially liquid hydrocarbons. The conversion of natural gas to higher order hydrocarbons, especially ethane and ethylene, would retain the material's versatility for use as precursor materials in chemical processing.

Known dehydrogenation and polymerization processes are available for the further conversion of ethane and ethylene to liquid hydrocarbons. In this way, easily transportable commodities may be derived directly from natural gas at the wellhead. A drawback in implementing such processes however has been in obtaining an efficient process for converting natural gas to higher order hydrocarbons.

The utilization of methane has been identified and targeted as one of the most important challenges facing the catalysis community today. This emphasis is not mislaid since methane represents a considerable source of energy and carbon atoms which could be used to assemble larger hydrocarbons or their derivatives.

Methane is the principal component of natural gas, which is composed of an admixture of normally gaseous hydrocarbons ranging from $C_1$ to $C_4$ and thus consists principally of methane admixed with ethane, propane, butane and other saturated, and some unsaturated hydrocarbons. Even though natural gas contains components higher boiling than methane, and such mixtures can be liquified at somewhat higher temperatures than pure methane, the temperatures required for condensation of the admixture is nonetheless too low for natural gas to be liquified and shipped economically. Under these circumstances the natural gas is not even of sufficient value for use as fuel, and it is wasted.

The conversion of methane to a useful liquid fuel would thus be attractive proposition. However, the only industrially feasible technology available today for this conversion is the Mobil process which is operational in New Zealand, where a unique combination of economic factors makes the conversion feasible. Elsewhere however, the energy limitations imposed by this multi-stage process and the additional burden of the Schulz-Flory distribution of products makes the process unsuitable.

Currently there is no known catalyst which provide an economical process capable of converting methane to higher hydrocarbons in a single step catalytic reaction. The Mobil process requires three catalytic reaction steps to transform methane into higher hydrocarbons and is thus of limited use.

The first step of the Mobil process involves the partial combustion of methane to produce carbon monoxide and hydrogen. The second step involves the synthesis of methanol from the carbon monoxide and hydrogen using a copper zinc catalyst at high pressures and low conversions per pass. The third step involves the conversion of the methanol to higher hydrocarbons and water over a zeolite catalyst. Such a multi-stage process is only economically feasible if a rare combination of economic factors are present.

For these reasons process streams which contain methane are usually burned as fuel. The thought of utilizing methane, particularly avoiding the tremendous and absolute waste of a natural resource in the manner outlined above, has challenged many minds; but has produced few solutions.

It would be highly desirable to be able to efficiently convert methane to hydrocarbons of higher molecular weight than methane (hereinafter, $C_2+$) particularly admixtures of $C_2+$ hydrocarbon products which can be economically liquified at remote sites; especially admixtures of $C_2+$ hydrocarbons rich in ethylene Ethylene is known to be a particularly valuable chemical raw materials for use in the petroleum, petrochemical, pharmaceutical, plastics and heavy chemicals industries. Ethylene is thus useful for the production of ethyl and ethylene compounds including ethyl alcohol, ethyl ethers, ethylbenzene, styrene, ethylene oxide, ethylene dichloride, ethylene dibromide, acetic acid, polyethylene and the like.

It has been long known that methane, and natural gas could be pyrolytically converted to $C_2+$ hydrocarbons. For example, methane or natural gas passed through a porcelain tube at moderate red heat will produce ethylene and its more condensed homologues such as propylene, as well as small amounts of acetylene and ethane.

These processes characteristically require considerable heat energy which, most often, is obtained from combustion of the by-product gases. The extreme temperatures make the operation of such processes uneconomical and, of course, serious materials problems are generally encountered. Numerous attempts have been made to catalyze these reactions at lower and more feasible temperatures, but such attempts have met with failure.

In all such processes of converting methane to $C_2+$ hydrocarbons a partial oxidation mechanism is involved, because hydrogen must be removed either as water, molecular hydrogen or other hydrogen containing specie. Likewise, any other polymerization mechanism in which the methane is converted to $C_2+$ hydrocarbons products requires a tremendous amount of energy, most often supplied as heat, to provide the driving force for the reactions.

In the past the molecular hydrogen liberated by the reaction has often been burned to provide the necessary process heat. This route has proven an abomination to the production of $C_2+$ hydrocarbons, but alternate reaction pathways have been little better because they have resulted in the production of large quantities of the higher, less useful hydrogen deficient polymeric materials such as coke, and highly oxidized products such as carbon dioxide and water.

The conversion of methane to higher order hydrocarbons at high temperatures, in excess of about 1200° C. is thus known. These processes are, however, energy intensive and have not been developed to the point where high yields are obtained even with the use of catalysts. And some catalysts that are useful in these processes (e.g., chlorine) are corrosive under such operating conditions.

The catalytic oxidative coupling of methane at atmospheric pressure and temperatures of from about 500° to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysts* 73, 9–19 (1982).

This article discloses the use of single component oxide catalysts that exhibited methane conversion to higher order hydrocarbons at rates no greater than four percent. The process by which Keller and Bhasin oxidized methane was cyclic, varying the feed composition between methane, nitrogen and air (oxygen) to obtain higher selectivities.

West German Pat. No. DE 32370792 discloses the use of a single supported component oxide catalysts. The process taught by this reference utilizes low oxygen partial pressure to give a high selectivity for the formation of ethane and ethylene. The conversion of methane to ethane and ethylene is, however, only on the order of from about four to about seven percent.

Methods for converting methane to higher order hydrocarbons at temperatures in the range of about 500° to about 1000° C. are disclosed in U.S. Pat. Nos. 4,443,644; 4,443,645; 4,443,646; 4,443,647; 4,443,648; and 4,443,648. The processes taught by these references provide relatively high selectivites to higher order hydrocarbons but at relatively low conversion rates, on the order of less than about four percent overall conversion.

In addition to synthesizing hydrocarbons, the processes disclosed in these references also produced a reduced metal oxide which must be frequently regenerated by contact with oxygen. The preferred processes taught by these references entail physically separate zones for a methane contacting step and for an oxygen contacting step, with the reaction promoter recirculating between the two zones.

U.S. Pat. Nos. 4,495,374 and 4,499,322 disclose processes for converting methane to higher order hydrocarbons using an oxidative synthesizing agent containing an alkali metal or compound thereof as a promoter. Both patents indicate that stability of the promoted synthesizing agent is enhanced by the presence of phosphorous.

While the direct dehydrogenative coupling of methane to higher hydrocarbons is thermodynamically infeasible below 1500° K., the oxidative coupling scheme were water is formed in addition to hydrocarbons suffers from no such restraints. However, the best results in the literature to date display modest ($\leq 5\%$) conversions at extremely high temperatures ($\geq 710$° C.), with a large amount of the methane being oxidized to $CO_2$ and CO.

Some catalysts containing iron, phosphorus and oxygen are known. Some of these have been used in the oxidation of some hydrocarbons, but not in the transformation of methane to $C_2+$ hydrocarbons.

There is therefore a strongly felt need for an efficient process for converting methane into useful products, for example, higher hydrocarbons, e.g. ethylene, ethane, or aromatic compounds.

SUMMARY OF THE INVENTION

Accordingly, it is an object of this invention to provide a new process for converting methane to higher hydrocarbons.

It is another object of this invention to provide a new process for converting methane to higher alkanes, alkenes and/or aromatic compounds.

It is another object of this invention to provide a new catalyst for converting methane to higher hydrocarbons.

It is another object of this invention to provide a new catalyst for converting methane to higher alkanes, alkenes and/or aromatic compounds.

The inventors have now discovered a new process and a new catalyst which satisfy all of the above objects of this invention, and other objects which will become apparent from the description of the invention given hereinbelow. The process uses a novel iron, phosphorous and oxygen-containing catalyst to convert methane, in the presence of dioxygen, to higher hydrocarbons. The catalyst used is an iron-phosphorous-oxide catalyst which possesses an iron to phosphorus ratio of from 0.1:1.0 to 2.0:1.0. The iron-phosphorous-oxide catalyst is contacted with methane and dioxygen ($O_2$) to transform the methane into $C_2+$ hydrocarbons.

BRIEF DESCRIPTION OF THE FIGURE

The FIGURE is the X-ray diffraction spectra of an unsupported Fe:P:O catalyst (Fe:P ratio=0.595:1.0). Arrows indicate the characteristic peaks of iron pyrophosphate.

DETAILED DESCRIPTION OF THE PREFERRED EMBODIMENTS

Figure 1:
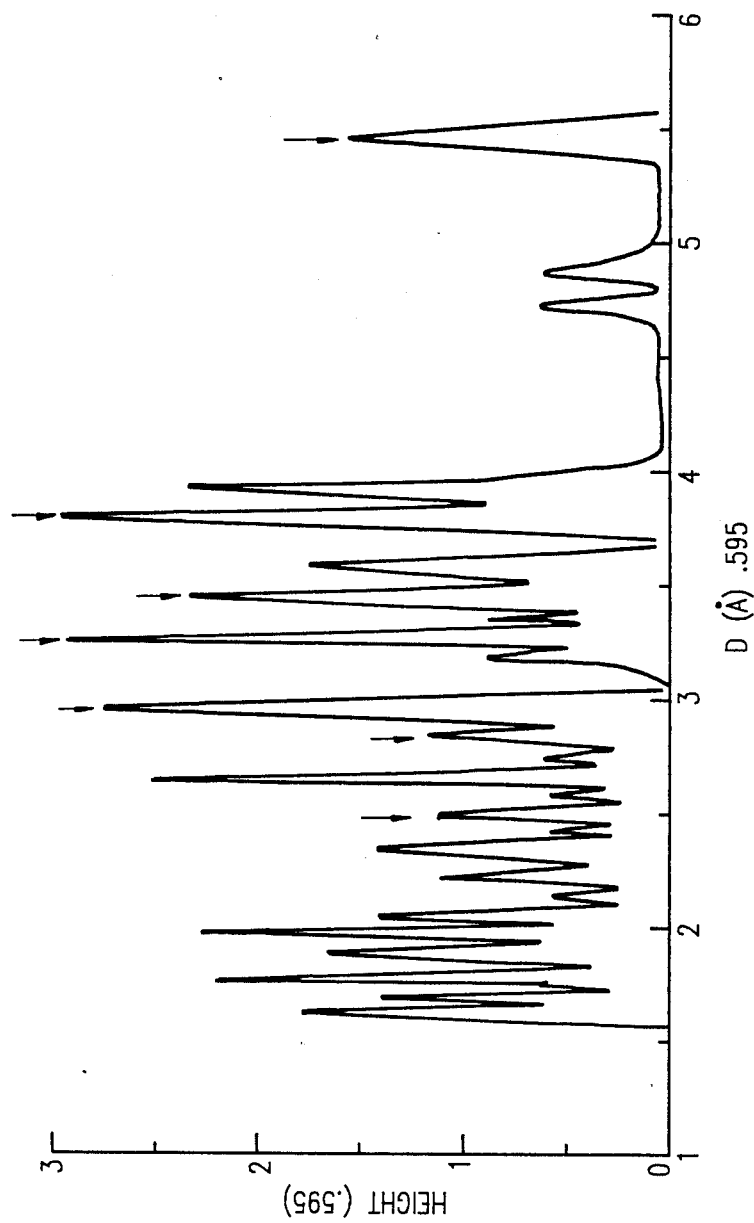

The catalyst of this invention permits methane conversions, via oxidative coupling, to higher hydrocarbons with very high selectivity (only very low amounts of CO or $CO_2$ are found in the product) at temperatures at least 200° C. lower than the lowest temperature reported in the literature. The process of this invention advantageously converts methane to other hydrocarbons, including aromatic compounds, quantitatively in only one step with no intermediate separation operation being required.

In comparison to other existing methods, the process of this invention is notably superior for the following reasons:

(i) the operating temperature required is much lower;

(ii) all of the methane is converted to higher hydrocarbons at low conversions;

(iii) the present process achieves very high selectivities (approaching 90% to $C_2$) and very high overall yields;

(iv) the primary products of this process, $C_2$ hydrocarbons, are the main raw materials needed by the chemical industry for synthesizing other valuable polymers and chemicals;

(v) on the basis of the cost of the raw materials required, the present process is economically feasible even in open market countries such as the U.S.A.; and (vi) very little, if any, methane is wasted to combustion products such as $CO_2$ or CO.

Sources of methane usable in the present invention

The methane used in the present invention can come from any known source. Pure methane or a methane-containing gas, such as natural gas can be used.

A major source of methane which can be used in this invention is natural gas which typically contains about 85% methane and about 10% ethane with the balance being made up of propane, the butanes, the pentanes and nitrogen.

Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from any of these sources and which is sometimes utilized as a fuel at the site can be used in this invention.

Prior to commercial use, natural gas is generally processed to remove water vapor, condensible hydrocarbons and inert or poisonous constituents. A so-treated product can also be used in this invention but there is no requirement that the methane-containing gas be pretreated before it is used.

To facilitate the process and prevent undue catalyst poisoning however, any notorious catalyst poison known to be in the gas can be removed in a known manner to provide a more efficient process.

Condensible hydrocarbons are generally removed from natural gas by cooling the natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station.

Processed natural gas typically comprises a major amount of methane, and minor amounts of ethane, propane, the butanes, the pentanes carbon dioxide and nitrogen. Generally, processed natural gas comprises from about 50% to more than about 95% by volume of methane. Such natural gas which is used principally as a source of heat in residential, commercial and industrial service can be used in the present invention.

The oxidant used in the present invention

In the process of this invention, dioxygen is used as the oxidizing species. This material can be used either in pure form or diluted in an inner gas, e.g., air can be used. The dioxygen or air can also be mixed with the methane prior to the reaction.

The reaction possesses multiple steady states, and high activities are obtained under the high steady state condition. The inventors have not succeeded in achieving the high steady state when the oxidant is diluted. However, the low steady state is achievable, and any inert gas can be used: nitrogen, argon, helium, etc. By the same token, air is useful as the oxidizing agent for low-steady-state operation. While the activities are not high in this regime, this is the regime where the periodic product separation is done. So, diluted oxidants can be used there.

Products obtained

The products of the present process are hydrocarbons. Normally the $C_2$ hydrocarbons make up over 80% of the higher hydrocarbons produced. The exact percentage depends on the temperature in feed composition.

The reaction exhibits a rate and selectivity bifurcation in temperature space. For example it was found that initially, at 575° C., the rate is very low, conversions are on the order of 0.1% of methane with an ethane selectivity of ca. 100% at a gas hourly space velocity of 28,000 $hr^{-1}$. As the temperature was increased, the rate increased, until at 725° C., the conversion was roughly 15 to 18% of the methane, with a $C_2$ selectivity of around 35%. Lowering the temperature to 575° C. now caused the rate to drop, but only slightly. This is termed the high steady state, and typical yields at the same space velocity as above are 11% conversion with 43% selectivity.

Under high conversion conditions the product distribution for $C_2$, $C_3$ and $C_4$ hydrocarbons obey a Schulz Flory-type relationship with a chain propagation probability of approximately 0.20.

After long periods of operation higher hydrocarbons, and aromatic compounds also appear in the product stream but the overall concentration is not very high and the distribution is no longer Schulz Flory type. Higher hydrocarbons are formed along with aromatics when the reaction is operated at higher pressures.

The above description of temperature effects was for a reactor pressure of 36 psig. Operating at 50 psig promotes higher chain propagation probabilities and formation of aromatics.

The olefin to parafin ratio of the products can be varied by decreasing the methane to oxygen ratio feed.

In general, the olefin-paraffin and hydrocarbonoxide ratios are dependent on the total conversion. The reaction rate is of positive order in $CH_4$ and $O_2$ partial pressure in the low steady state. In the high steady state, the reaction is sustained only over a small range of gas phase mole fractions, but it appears that the rate is of zero order in $CH_4$ while preserving its positive order in $O_2$. Under high conversions, as in the high steady state, typical selectivities are 43% hydrocarbons as indicated earlier, and the olefin: paraffin ratio is typically 0.65.

The catalyst

The catalyst used in this invention is an iron-phosphorus-oxide (Fe—P—O) catalyst. The Fe—P—O catalyst can be prepared by preparing an aqueous slurry of (1) ferric nitrate and/or ferric ammonium nitrate and (2) phosphoric acid and/or an alkali metal phosphate, e.g. sodium phosphate, potassium phosphate or lithium phosphate. To prepare this slurry one may use, for example, 75 ml of water, 2 grams of support and appropriate amounts of the iron component and the phosphorous component to obtain the desired loading. The aqueous slurry is stirred vigorously at room temperature, keeping a steady pH of 4 to 5. A high surface area support is then added to the solution with the vigorous stirring being maintained. The resulting slurry is then dried in an air atmosphere to provide a catalyst precursor powder. The final catalyst is then obtained by heating at a temperature of above 300° C., e.g. 525° to 625° C., preferably 560° to 590° C., the catalyst precursor in a dioxygen-containing gas, e.g. air or pure dioxygen.

Supported Fe—P—O catalysts useful in this invention can be produced by mechanical mixing of solid components, or precipitation and adsorption onto the support from an organic solution. The activity levels depend on the surface area of the catalyst.

The catalysts of the present invention must be activated by subjecting them to a sufficiently high temperature of at least 725° C. While the reason for this activation is not currently understood, the inventors have noted that the unactivated catalysts (catalysts which have not been subjected to a sufficiently high temperature) do not have the characteristic X-ray diffraction spectra of the active catalyst of identical composition, and thus it appears that the activation is due to temperature hysteresis. Further, they have noted that such unactivated catalysts seem to be primarily amorphous in nature. Attempts to use pure iron-phosphorus-oxygen compounds of various kinds as catalyst have not been successful.

The inventors have identified by X-ray diffraction (see the FIGURE) that there is a unique component in the active composition of their Fe—P—O catalysts. This unique component is ferric pyrophosphate (see arrows in FIGURE) in conjunction with a stabilizing agent which furthers the stability of their catalysts under the reaction conditions. The pyrophosphate and the stabilizing agent are formed as a result of the catalyst preparation procedure. The existence of these phases is unique to the active compositions of the catalyst.

A reliable means of using the catalyst of this invention comprises loading an active composition in a reactor, running a co-feed reaction with methane and dioxygen at an elevated temperature of, for example 700° C. to 800° C., and then cooling the reactor down while running the co-feed to 550° to 600° C., for example 575° C. The reaction then continues at a rate comparable to the rate at the elevated temperature for an indefinite amount of time.

The oxygen content of the catalysts is not yet known. However, there is evidence that oxygen reservoirs are built up in the catalyst during the reaction. This oxygen is different from gaseous oxygen in that it is highly active in forming $C_2$ products but is incapable of forming oxide products.

A number of supports can be used. They include alumina, titania and mixtures thereof as well as other materials including various silicas. Catalyst supports which can be used include, e.g., Cab-O-sil silica. A good loading range is 1 to 90%, preferably 3–20% and most preferably 4–10%.

Supporting the catalyst on silica has a profound effect on its activity stability. While the Fe:P ratios of the most active and selective supported catalyst correspond well with similar figures on the unsupported catalyst, a wider range of active compositions was found to exist.

Unsupported catalyst having Fe:P mole ratios of from 0.6:1.0 to 0.67:1.0 were found to be active. Supported catalysts with Fe:P mole ratio 0.4:1.0 to 1.0:1.0 were found to possess activity. However, the most active catalysts which were supported were those with Fe:P mole ratios of from 0.6:1.0 to 0.67:1.0.

The mole ratio of iron to phosphorous in the catalyst is thus important. This ratio should fall within the range of 0.1:1.0 to 2.0:1.0, preferably 0.45:1.0 to 1.4:1.0, most preferably 0.55:1.0 to 0.75:1.0.

Reactor operating conditions

The process of the present invention oxidatively couples methane to ethylene and ethane. In this process a mixture of methane and oxygen or air is passed over a Fe—P—O catalyst. Products such as carbon monoxide and carbon dioxide can be separated from the ethane and ethylene products by operating the reactor in a cyclic manner involving sequential treatment of the Fe—P—O catalyst with methane and oxygen or air.

Sequential separation is possible at low conversions as follows. Initially, pure oxygen is passed over the catalyst. This causes oxygen incorporation into the catalyst. Then, the feed is switched to pure methane, causing the oxygen in the catalyst to be reacted off. This oxygen is incapable of forming CO and $CO_2$, while it is active in forming $C_2$ products. During this phase, the reactor off-gases are directed by a 3-way valve to a reservoir which will thus store almost pure hydrocarbon products. When the feed is switched back to oxygen, any carbonaceous species left on the catalyst are burned off, forming CO and $CO_2$ almost exclusively, with very small quantities of $C_2$ hydrocarbons being formed.

The process of the present invention can be run either as a batch or preferably as a continuous process. A continuous processes with (1) alternating methane and oxygen feeds separated by a purge feed of inert gas such as argon or nitrogen and (2) continuous co-feed of methane and oxygen can be used for example.

For the conversion of methane to $C_{2+}$ hydrocarbons, the conversion is highest close to the explosive mixture limit, for which the methane concentration in methane/oxygen mixtures is 58 volume percent. For purposes of safety, it is desirable to operate as close to this methane concentration while staying above the limiting concentration. As the methane to oxygen ratio increases, the conversion decreases and the paraffin to olefin ratio increases.

The suitable concentration ranges of operation are therefore 50 to 99% methane, preferably 60 to 75% and most preferably 62 to 68%. Preferred temperatures of operation for the alternating feed process are 500° to 700° C. and most preferably 550° to 590° C. Preferable conditions for the co-feed process are as described supra. Preferable pressure conditions for the process are around 45 to 50 psig, or higher.

The catalyst selectivity is a strong function of temperature and a critical temperature can be observed in the range of 520° to 550° C. in which the catalyst slowly deactivates. Above 560° C. the activity of the catalyst can be maintained for long periods of time. Accordingly, in the process of the present invention a temperature of at least 550° C. is preferably used, and although there is no strict upper limit, it is most perferred that a temperature of from 550° C. to 1500° C. be used.

Other features of the invention will become apparent in the course of the following descriptions of exemplary embodiments which are given for illustration of the invention and are not intended to be limiting thereof.

Example

An Fe:P:O catalyst was prepared by dissolving 5.25 grams of ferric nitrate in an excess of water and adding 2.49 grams of an 80% solution of phosphoric acid to the solution. After vigorous stirring at room temperature, 5 grams of high surface area silica was added to the solution and stirred. The resulting slurry was dried at 75° C. in an air atmosphere and the resulting powder constituted the catalyst precursor. 0.1 grams of the catalyst precursor was loaded into a quartz reactor and held tightly between quartz wool plugs. The precursor was treated with dioxygen at 575° C. for 8 hours. Passing a mixture of methane and dioxygen over this catalyst at 575° C. resulted in a conversion of approximately 0.2% to $C_2$ hydrocarbons. $C_2$ selectivity at this stage was around 93%. Raising the temperature to 725° C. resulted in a conversion of 8.5% to $C_2$ hydrocarbons and a selectivity of 35%. Lowering of the temperature of this reaction process to 575° C. resulted in a conversion and selectivity different than the original values at 575° C. These values were a 6% $C_2$ conversion and a 43% selectivity.

A further experiment consisted of flowing, over the catalyst, in sequence, methane, argon, dioxygen, and argon, and repeating this sequence cyclically. The argon was flowed for 100 seconds, the dioxygen for 200 seconds and the methane for times from 200 to 2000 seconds. It was observed that the changeover from a methane step to a dioxygen step (with the argon step in between) resulted in a mixture of carbon oxides and $C_2$ hydrocarbons being formed. However, the changeover from dioxygen to methane with the argon step in between resulted in formation of almost pure $C_2$ hydrocarbons. Typical conversions of $C_2$ hydrocarbons during these steps amounted to about 1%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A supported iron:phosphorous:oxide catalyst composition, wherein said catalyst has an Fe:P molar ratio of 0.1:1.0 to 2.0:1.0, said supported catalyst being obtained by a process comprising:
   (i) combining (ia) ferric nitrate or ferric ammonium nitrate and (ib) phosphoric acid or an alkali metal phosphate in an amount of water sufficient to obtain a slurry;
   (ii) adding to the slurry, under stirring, a catalyst support;
   (iii) drying the slurry of step (ii) in air to obtain a catalyst precursor; and
   (iv) heating the catalyst precursor to a temperature of at least 725° C. in a dioxygen-containing gas to activate said catalyst precursor and obtain said catalyst.

2. The supported catalyst in claim 1, wherein said catalyst contains a ferric pyrophosphate component.

3. The supported catalyst of claim 1, wherein said catalyst has an Fe:P molar ratio of from 0.1:1.0 to 1.0:1.0.

4. The supported catalyst of claim 3, wherein said ratio is 0.55:1.0 to 0.75:1.0.

5. The supported catalyst of claim 1, comprising combining ferric nitrate and phosphoric acid in step (i).

6. The supported catalyst of claim 1, comprising combining ferric nitrate and an alkali metal phosphate in step (i).

7. The supported catalyst of claim 1, comprising combining ferric ammonium nitrate and phosphoric acid in step (i).

8. The supported catalyst of claim 1, comprising combining ferric ammonium nitrate and an alkali metal phosphate in step (i).

9. The supported catalyst of claim 1, wherein said catalyst support is alumina, titania, a mixture of alumina and titania, or a silica.

10. The supported catalyst of claim 1, wherein said catalyst support is a silica.

11. The supported catalyst of claim 1, wherein said catalyst is present in an amount of from 1 to 90% of the support.

12. The supported catalyst of claim 1, wherein said catalyst is present in an amount of from 3 to 20% on said support.

13. The supported catalyst of claim 1, wherein said catalyst is present in an amount of from 4 to 10% on said support.

14. The supported catalyst of claim 1, wherein said catalyst has an Fe:P molar ratio of from 0.6:1.0 to 0.67:1.0.

15. An iron:phosphorous:oxide catalyst composition having an Fe:P molar ratio of 0.1:1.0 to 2.0:1.0 and being obtained by a process comprising:
   (i) combining (ia) ferric nitrate or ferric ammonium nitrate and (ib) phosphoric acid or an alkali metal phosphate in an amount of water sufficient to obtain a slurry;
   (ii) stirring the slurry of step (i);
   (iii) drying the slurry of step (ii) in air to obtain a catalyst precursor; and
   (iv) heating the catalyst precursor to a temperature of at least 725° C. in a dioxygen-containing gas to activate said catalyst precursor and obtain said catalyst.

16. The catalyst of claim 15, wherein said catalyst contains a ferric pyrophosphate component.

17. The catalyst of claim 15, wherein said catalyst has a Fe:P molar ratio of 0.6:1.0 to 0.67:1.0.

* * * * *

UNITED STATES PATENT AND TRADEMARK OFFICE
CERTIFICATE OF CORRECTION

PATENT NO. : 4,952,547
DATED : AUGUST 28, 1990
INVENTOR(S) : ANANTH V. ANNAPRAGADA, ET AL

It is certified that error appears in the above-identified patent and that said Letters Patent is hereby corrected as shown below:

Column 1, line 30; correct "artic" to read --arctic--.

Column 2, line 17; insert --an-- before "attractive".

Column 2, line 26; correct "provide" to read --provides--.

Column 2, line 53; insert --.-- after "ethylene".

Column 2, line 55; correct "materials" to read --material--.

Column 3, line 60; delete "4,443,648;".

Column 4, line 16; correct "were" to read --where--.

Column 6, line 57; correct "parafin" to read --paraffin--.

Column 8, line 45; correct "processes" to read --process--.

Signed and Sealed this

Seventeenth Day of March, 1992

Attest:

HARRY F. MANBECK, JR.

*Attesting Officer*   *Commissioner of Patents and Trademarks*

UNITED STATES PATENT AND TRADEMARK OFFICE
CERTIFICATE OF CORRECTION

PATENT NO. : 4,952,547
DATED : August 28, 1990
INVENTOR(S) : Annapragada, et. al.

It is certified that error appears in the above-identified patent and that said Letters Patent is hereby corrected as shown below:

Column 1, between "CATALYST FOR CONVERTING METHANE

TO HIGHER HYDROCARBONS, INCLUDING AROMATIC COMPOUNDS"

and "BACKGROUND OF THE INVENTION", insert the following:

--This invention was made with Government support under Grant

CBT85-13127 awarded by the National Science Foundation. The

Government has certain rights in the invention.--

Signed and Sealed this

Fifteenth Day of December, 1992

*Attest:*

DOUGLAS B. COMER

*Attesting Officer*  *Acting Commissioner of Patents and Trademarks*